United States Patent
Rubaek et al.

(10) Patent No.: US 11,701,442 B2
(45) Date of Patent: Jul. 18, 2023

(54) METHOD OF AUTONOMOUS MOBILE DISINFECTION

(71) Applicant: UVD Robots Aps, Odense (DK)

(72) Inventors: Thomas Rubaek, Odense (DK); Efraim Vitzrabin, Odense (DK); John Erland Østergaard, Odense (DK); Rune K. Larsen, Odense (DK)

(73) Assignee: UVD Robots ApS, Odense (DK)

( * ) Notice: Subject to any disclaimer, the term of this patent is extended or adjusted under 35 U.S.C. 154(b) by 664 days.

(21) Appl. No.: 16/836,139

(22) Filed: Mar. 31, 2020

(65) Prior Publication Data
US 2021/0299295 A1    Sep. 30, 2021

(51) Int. Cl.
*A61L 2/10* (2006.01)
*A61L 2/24* (2006.01)

(52) U.S. Cl.
CPC .................... *A61L 2/10* (2013.01); *A61L 2/24* (2013.01); *A61L 2202/14* (2013.01); *A61L 2202/16* (2013.01); *A61L 2202/25* (2013.01); *A61L 2202/26* (2013.01)

(58) Field of Classification Search
CPC .......... A61L 2/10; A61L 2/24; A61L 2202/14; A61L 2202/16; A61L 2202/25; A61L 2202/26
See application file for complete search history.

(56) References Cited

U.S. PATENT DOCUMENTS

| 2012/0223216 A1* | 9/2012 | Flaherty | G05D 1/0242 |
| | | | 901/1 |
| 2016/0296649 A1* | 10/2016 | Ramanand | A61L 2/28 |
| 2017/0112954 A1* | 4/2017 | Dayton | A61L 9/20 |

FOREIGN PATENT DOCUMENTS

| TW | 200902099 A | 1/2009 |
| WO | 2013106077 A2 | 7/2013 |
| WO | 2019079065 A1 | 4/2019 |

OTHER PUBLICATIONS

Taiwanese Office Action issued in TW109111655, dated Mar. 29, 2022, 4 pages.
Taiwanese Office Action issued in TW109111655, dated Jul. 13, 2022, 2 pages.

* cited by examiner

*Primary Examiner* — Sean E Conley
(74) *Attorney, Agent, or Firm* — Kevin Roddy; Butzel Long

(57) ABSTRACT

Implementations of the disclosed subject matter provide a method of receiving, at an actuated mobile device, at least one dosage level for a predetermined area, where the at least one dosage level is based on a first dosage of ultraviolet (UV) light to be output from at least one light source for at least a portion of the predetermined area. The method may include moving the actuated mobile device in a path within the predetermined area and outputting the UV light from the at least one light source onto one or more first surfaces based on the received at least one dosage level. The method may include moving the actuated mobile device within the path, and outputting the UV light onto one or more second surfaces based on the received at least one dosage level.

18 Claims, 13 Drawing Sheets

METHOD OF AUTONOMOUS MOBILE DISINFECTION

BACKGROUND

Mobile devices, such as mobile robots, can be operated so as to disinfect indoor areas, such as a room that have an unclean surfaces. Typically, such devices do not disinfect an area in an efficient manner, and may fail to disinfect all contaminated surfaces.

BRIEF SUMMARY

According to an implementation of the disclosed subject matter, a method may be provided that includes an actuated mobile device to receive at least one dosage level for a predetermined area, where the at least one dosage level is based on a first dosage of ultraviolet (UV) light to be output from at least one light source of the actuated mobile device or another actuated mobile device for at least a portion of the predetermined area. The method may include moving the actuated mobile device in a path within the predetermined area and outputting the UV light from the at least one light source onto one or more first surfaces based on the received at least one dosage level. The method may include moving the actuated mobile device within the path, and outputting the UV light onto one or more second surfaces based on the received at least one dosage level.

Additional features, advantages, and implementations of the disclosed subject matter may be set forth or apparent from consideration of the following detailed description, drawings, and claims. Moreover, it is to be understood that both the foregoing summary and the following detailed description are illustrative and are intended to provide further explanation without limiting the scope of the claims.

BRIEF DESCRIPTION OF THE DRAWINGS

The accompanying drawings, which are included to provide a further understanding of the disclosed subject matter, are incorporated in and constitute a part of this specification. The drawings also illustrate implementations of the disclosed subject matter and together with the detailed description serve to explain the principles of implementations of the disclosed subject matter. No attempt is made to show structural details in more detail than may be necessary for a fundamental understanding of the disclosed subject matter and various ways in which it may be practiced.

DETAILED DESCRIPTION

Figure 1:
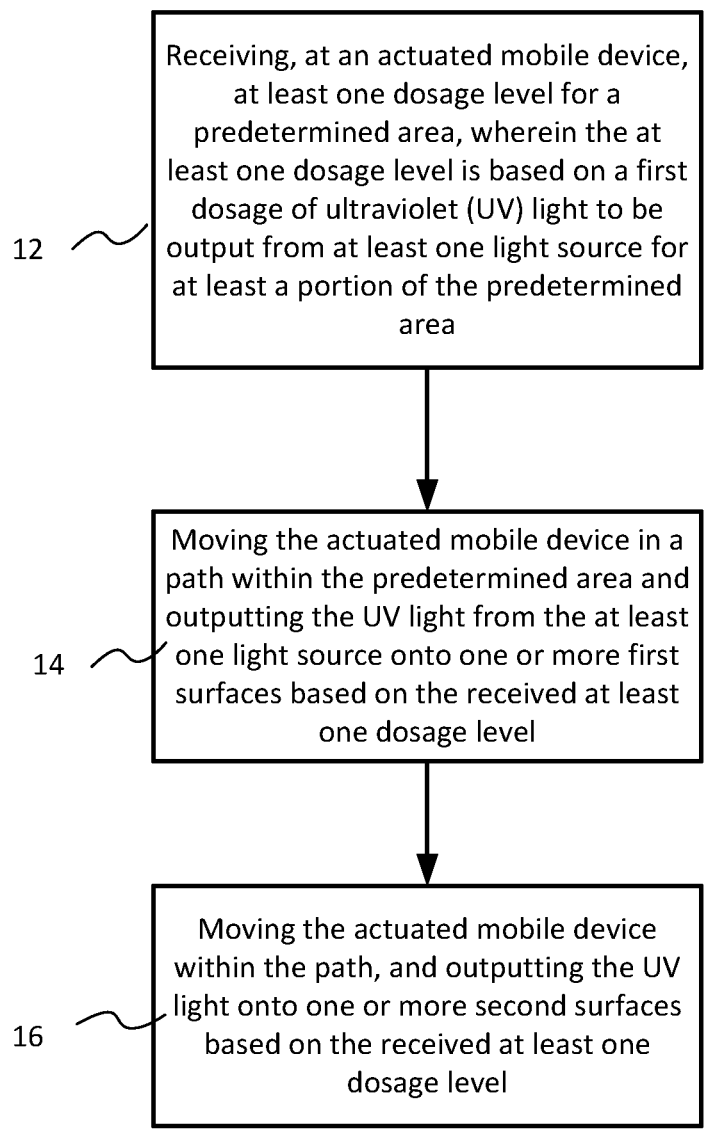
FIG. 1 shows an example method of moving an actuated mobile device within a predetermined area and outputting ultraviolet (UV) light having a dosage level to disinfect the predetermined area according to an implementation of the disclosed subject matter.

An actuated mobile device, such as a mobile robot, may be used to disinfect a predetermined area such as a room, a building, surfaces, air, objects, or the like in an environment using ultraviolet (UV) light from a light source. The actuated mobile device may receive, via a user interface and/or a network interface, at least one dosage level for the predetermined area. For example, the dosage level may be based on a first dosage of UV light to be output from the light source of the actuated mobile device.

In some implementations, the actuated mobile device may autonomously enter the predetermined area, and may output UV light based on the received dosage level to disinfect the area. The actuated mobile device may have a map of the area stored in memory, may receive the map via a network interface, and/or may map the area using one or more sensors. The actuated mobile robot may receive a path via the network interface and/or determine a path to move within the area and to disinfect the area by outputting UV light from the light source. The path may be selected and/or determined so as to minimize the amount of time to apply the dosage level of UV light and disinfect the area.

Progress of applying the dosage level of UV light may be monitored by generating an exposure plot of the portions of the area that have been disinfected. In some implementations, the actuated mobile device may determine and/or detect portions of the area that have not received the dosage of UV light. For such portions, the actuated mobile device may adjust an arm with another light source to output UV light to the portion of the area. In some implementations, UV light may be output from the light source, and may be reflected from a reflective surface attached to a second actuated mobile device to provide the dosage of UV light to the portion of the area. In some implementations, two or more actuated mobile devices may be operated within the area to apply the dosage of UV light and disinfect the area in less time than a single actuated mobile device.

The actuated mobile device may be used as part of a regular cleaning cycle of a room, building, or the like, and may prevent and/or reduce the spread of infectious diseases, viruses, bacteria, and other types of harmful organic microorganisms in the environment by breaking down their DNA-structure with UV light. The actuated mobile device may reduce human error in cleaning an area, room, building, or the like by tracking the location and/or intensity (e.g., optical power of UV light) of light radiated, and determine which areas may need to be radiated and/or cleaned.

The actuated mobile device may be operated manually, autonomously, and/or may receive control signals to control the movement of the actuated mobile device with a room, building, area, or the like when operating in a tele-operation mode.

Traditional disinfection methods and devices using ultraviolet light require that a person enter a room or area with the device. With such methods and devices, the person may introduce new contaminants to the room or area. Other methods and devices use disinfectants such as wipes, chemicals, and the like. However, airborne particles may settle on the surface treated with the wipes and/or chemicals.

Implementations of the disclosed subject matter may deploy the actuated mobile device to a room, building, and/or area without putting a person (e.g., a member of a healthcare staff) at risk in a contaminated environment. That is, the actuated mobile device may disinfect air, surfaces, and/or objects without putting a member of the healthcare staff at risk, may reduce the costs of protective equipment for a person, may reduce time in disinfecting, and/or may provide a report which includes details of the surfaces and/or objects that have been disinfected.

FIG. 1 shows an example method 10 of moving an actuated mobile device within a predetermined area and outputting ultraviolet (UV) light having a dosage level to disinfect the predetermined area according to an implementation of the disclosed subject matter.

At operation 12, the actuated mobile device (e.g., actuated mobile device 100 shown in FIGS. 5-14) may receive at least one dosage level for a predetermined area. The dosage level may be received, for example, via a user interface (e.g., user interface 110 shown in FIG. 13) and/or via a network interface (e.g., network interface 116 shown in FIG. 13) of the actuated mobile device. The at least one dosage level may be based on a first dosage of ultraviolet (UV) light to be output from at least one light source (e.g., light source 104 shown in FIGS. 5, 7, 9-11, and 13) for at least a portion of the predetermined area (e.g., room 210 shown in FIGS. 8, 9, 11, and 12).

At operation 14, the actuated mobile device may be moved in a path (e.g., path 212 shown in FIG. 8) within the predetermined area (e.g., room 210 shown in FIGS. 8, 9, 11, and 12). The UV light may be output from the at least one light source (e.g., light source 104 shown in FIGS. 5, 7, 9-11, and 13), onto one or more first surfaces (e.g., surfaces 300, 302, 304 shown in FIGS. 8, 9, 11, and 12; objects 306, 308, 312, 314 shown in FIGS. 8, 9, 11, 12; and/or reference tag 310 shown in FIG. 9) based on the received at least one dosage level.

Figure 8:
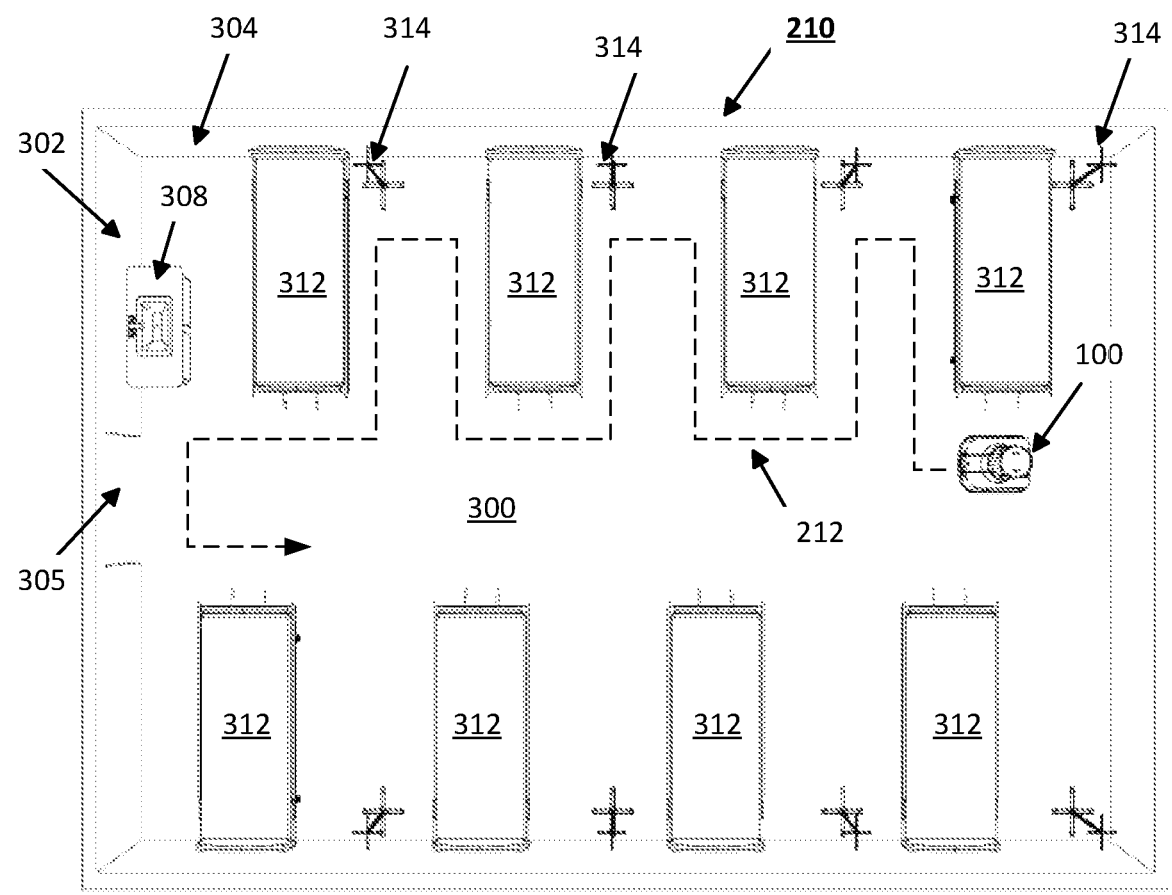
FIG. 8 shows an example of a path of the actuated mobile device to apply a dosage of UV light in an area according to an implementation of the disclosed subject matter.

In some implementations, a processor communicatively coupled to the actuated mobile device may determine the path (e.g., path 212 shown in FIG. 8) of the actuated mobile device. For example, as shown in FIG. 8, the processor may determine the path 212 for the actuated mobile device 100 in room 210, having walls (e.g., surfaces 302, 304), floor (e.g., surface 300), object 308 (e.g., a sink), object 312 (e.g., a bed), object 314 (e.g., 4-hook IV stand), and the like. The path may be determined so that the actuated mobile device may output a dosage of UV light to the objects 308, 312, 314, and the surfaces 300, 302, 304 to disinfect them in, for example, the shortest amount of time. The processor may be, for example, controller 114 shown in FIG. 13, and/or server 140 and/or remote platform 160 which may be communicatively coupled to the actuated mobile device 100 via the network 130 as shown in FIG. 14. In some implementations, the determined path may be a random path.

Figure 9:
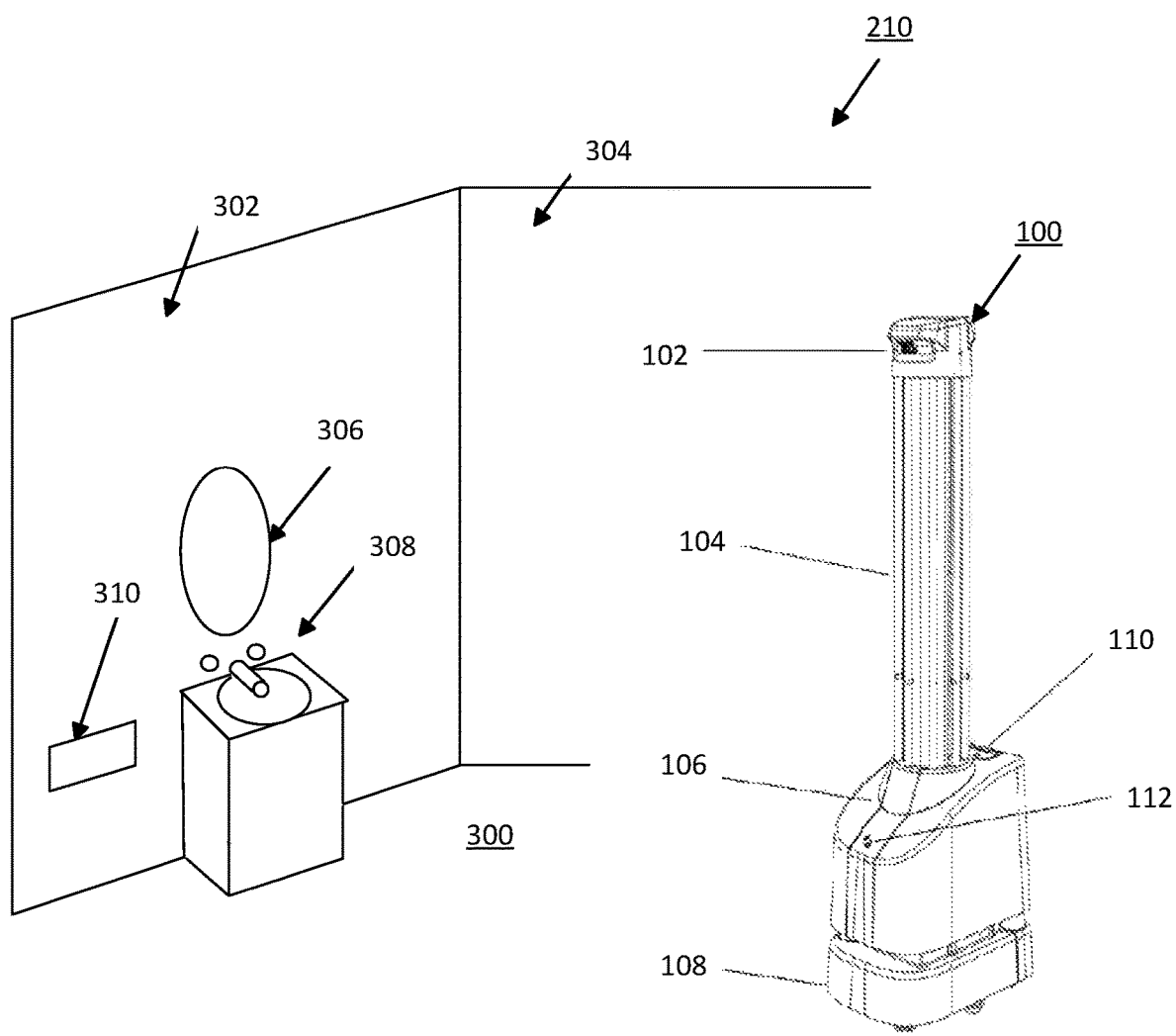
FIG. 9 shows an example of the actuated mobile device outputting UV light onto surfaces, objects, hotspots, and/or reference tags of an area to disinfect them according to an implementation of the disclosed subject matter.
Figure 10:
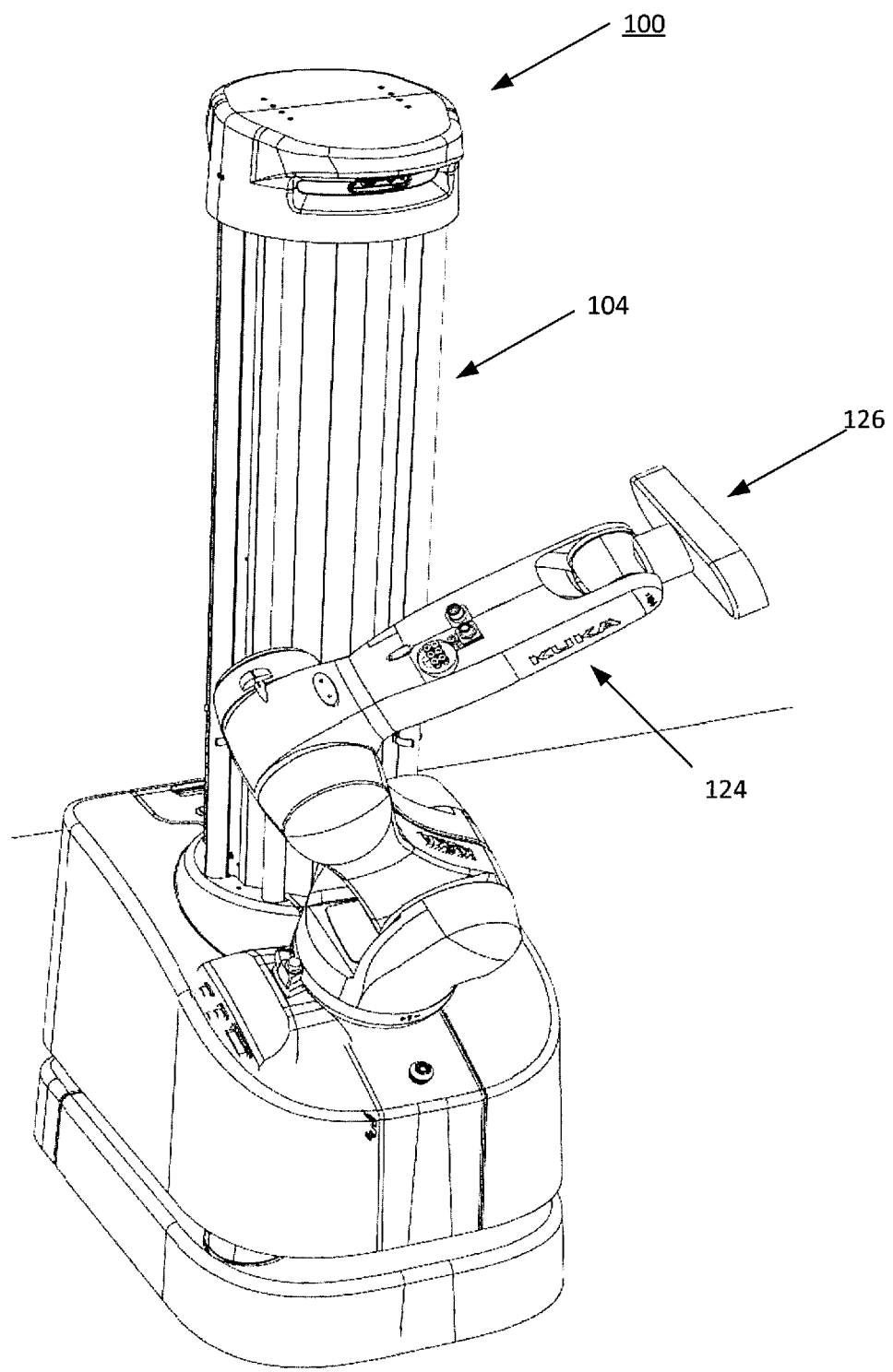
FIG. 10 shows the actuated mobile device that includes a second UV light source coupled to an arm according to an implementations of the disclosed subject matter.

In some implementations, the path (e.g., path 212 shown in FIG. 8) may be determined based on an environment of the predetermined area (e.g., room 210 shown in FIGS. 8, 9, 11, and 12), providing a reduced time for disinfection of the predetermined area, and/or increasing the dosage to the one or more first surfaces and the one or more second surfaces (e.g., surfaces 300, 302, 304 shown in FIGS. 8, 9, 11, and 12; objects 306, 308, 312, 314 shown in FIGS. 8, 9, 11, 12; and/or reference tag 310 shown in FIG. 9).

The path may be determined, for example, based at least in part on a two dimensional map or a three-dimensional map generated by the processor (e.g., controller 114 shown in FIG. 13, and/or server 140 and/or remote platform 160 which may be communicatively coupled to the actuated mobile device 100 via the network 130 as shown in FIG. 14) and at least one sensor (e.g., sensor 102 and/or sensor 106) of the actuated mobile device moving within the predetermined area (e.g., room 210) at a previous point in time.

In some implementations, the path may be determined based on an amount of UV light that is to be output from the light source (e.g., light source 104) on the one or more first surfaces and the one or more second surfaces (e.g., surfaces 300, 302, 304 shown in FIGS. 8, 9, 11, and 12; objects 306, 308, 312, 314 shown in FIGS. 8, 9, 11, 12; and/or reference tag 310 shown in FIG. 9). In some implementations, the path may be a perimeter of the predetermined area (e.g., a perimeter of room 210 shown in FIGS. 8 and 12).

At operation 16, the actuated mobile device may be moved within the path (e.g., path 212 shown in FIG. 8), and may output the UV light onto one or more second surfaces (e.g., surfaces 300, 302, 304 shown in FIGS. 8, 9, 11, and 12; objects 306, 308, 312, 314 shown in FIGS. 8, 9, 11, 12; and/or reference tag 310 shown in FIG. 9) based on the received at least one dosage level. In some implementations, the moving the actuated mobile device within the path may include moving the actuated mobile device in a predetermined pattern (e.g., a grid pattern along a determined pattern within the predetermined area, or the like).

In some implementations, the method 10 may include using a processor communicatively coupled to the actuated mobile device (e.g., controller 114 shown in FIG. 13, and/or server 140 and/or remote platform 160 which may be communicatively coupled to the actuated mobile device 100 via the network 130 as shown in FIG. 14) to determine whether the one or more first surfaces and the one or more second surfaces (e.g., surfaces 300, 302, 304 shown in FIGS. 8, 9, 11, and 12; objects 306, 308, 312, 314 shown in FIGS. 8, 9, 11, 12; and/or reference tag 310 shown in FIG. 9) have received the first dosage. As discussed below, a second light source and/or a second actuated mobile device may be used to apply a dosage to objects, surfaces, and the like that may be determined as to not have received the first dosage.

In some implementations, the method 10 may include using a sensor (e.g., sensor 102, 106 shown in FIG. 5) of the actuated mobile device to detect at least one hotspot within the predetermined area (e.g., room 210). The hotspot may be a predetermined object (e.g., objects 306, 308, 312, 314 shown in FIGS. 8, 9, 11, and 12; and/or reference tag 310 shown in FIG. 9), at least a portion of the predetermined area (e.g., surfaces 300, 302, 304 shown in FIGS. 8, 9, 11, 12), and/or an object having a predetermined type of contaminant. For example, the at least one hotspot may be a chair, a seat, a bed, a sink, mirror, a door, a door handle, a wall, a floor, a ceiling, a shelf, a surface of a table, and any object and/or surface defined as the at least one hotspot in a memory (e.g., memory 118 and/or fixed storage 120 shown in FIG. 13; database 150 shown in FIG. 14) that is communicatively coupled to a processor (e.g., controller 114 shown in FIG. 13, and/or server 140 and/or remote platform 160 which may be communicatively coupled to the actuated mobile device 100 via the network 130 as shown in FIG. 14) of the actuated mobile device.

In some implementations, the UV light may be output from the at least one light source (e.g., light source 104 shown in FIG. 5) at a second dosage onto the at least one hotspot. This second dosage may be greater than the first dosage. That is, the intensity and/or duration of the UV light output to the hotspot based on the second dosage may be greater that the intensity and/or duration of the UV light output based on the first dosage.

Figure 2:
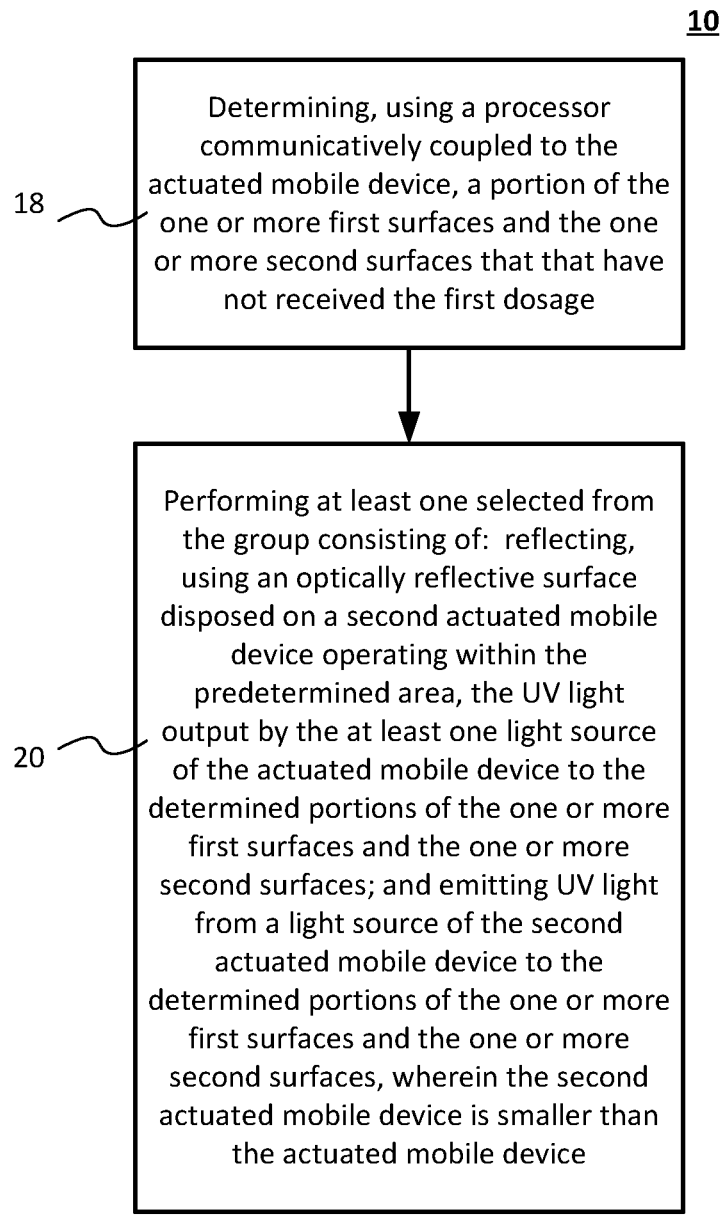
FIG. 2 shows the example method of FIG. 1 may include a method of determining which surfaces of the predetermined area have not received the dosage of UV light, and outputting UV light to the determined surfaces according to an implementation of the disclosed subject matter.

FIG. 2 shows that the example method 10 of FIG. 1 may include a method of determining which surfaces of the predetermined area have not received the dosage of UV light, and outputting UV light to the determined surfaces according to an implementation of the disclosed subject matter. At operation 18, a processor communicatively coupled to the actuated mobile device (e.g., controller 114 shown in FIG. 13, and/or server 140 and/or remote platform 160 which may be communicatively coupled to the actuated mobile device 100 via the network 130 as shown in FIG. 14) may determine a portion of the one or more first surfaces and the one or more second surfaces that that have not received the first dosage (e.g., surfaces 300, 302, 304 shown in FIGS. 8, 9, 11, and 12; objects 306, 308, 312, 314 shown in FIGS. 8, 9, 11, 12; and/or reference tag 310 shown in FIG. 9).

At operation 20, the actuated mobile device may perform one of more operations. For example, an optically reflective surface (e.g., reflective surface 202 shown in FIG. 11) disposed on a second actuated mobile device (e.g., actuated mobile device 200 shown in FIG. 11) operating within the predetermined area (e.g., room 210) may be used to reflect the UV light output by the at least one light source (e.g., light source 104) of the actuated mobile device (e.g., actuated mobile device 100 shown in FIG. 11) to the determined portions of the one or more first surfaces and the one or more second surfaces (e.g., surfaces 300, 302, 304 shown in FIGS. 8, 9, 11, and 12; objects 306, 308, 312, 314 shown in FIGS. 8, 9, 11, 12; and/or reference tag 310 shown in FIG. 9).

Figure 11:
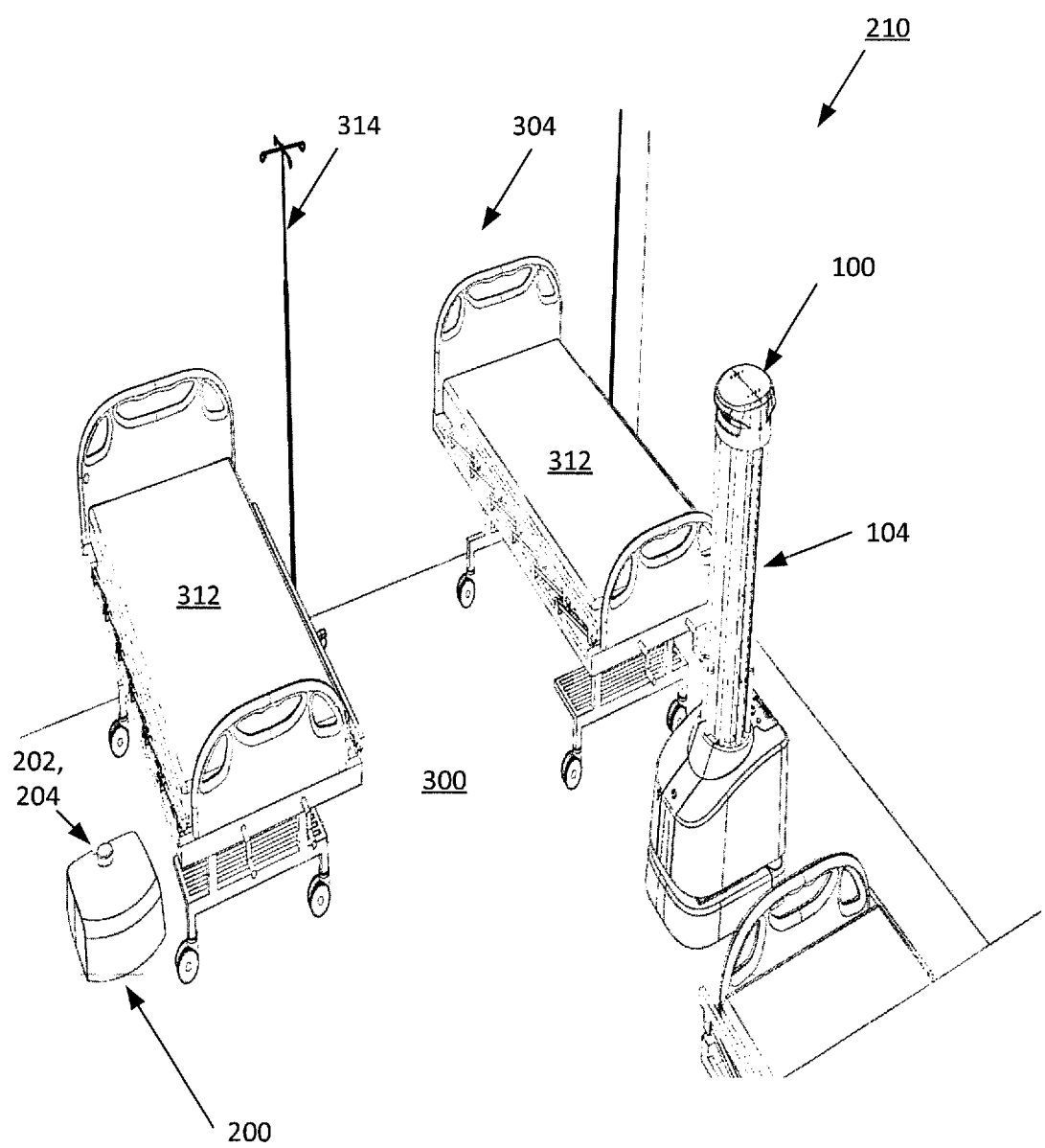
FIG. 11 shows an arrangement where a second actuated mobile device may reflect UV light output by the first actuated mobile device, and/or output a dosage of UV light from a light source according to implementations of the disclosed subject matter.

As shown in FIG. 11, the reflective surface 202 of the actuated mobile device 200 may reflect UV light output from the light source 104 of the actuated mobile device 100 into the air, onto a surface, and/or onto an object. The reflective surface may be a mirror, a reflective coating, and/or any other surface that may be reflective for UV light. For example, light emitted from the light source 104 may be reflected by the reflective surface 202 onto the objects 312, 314 and/or surface 300, 304 shown in FIG. 11 to disinfect these objects and/or surfaces with a dosage of UV light.

In some implementations, UV light may be from the light source of the second actuated mobile device (e.g., light source 204 of the actuated mobile device 200 shown in FIG. 11) to the determined portions of the one or more first surfaces and the one or more second surfaces. As shown in FIG. 11, the actuated mobile device 200 may include the light source 204, which may include one or more bulbs, one or more lamps, and/or an array of light emitting diodes (LEDs) or organic light emitting diodes (OLEDs) to emit UV light (e.g., light having a wavelength of 10 nm-400 nm). In some implementations, the light source 204 may provide a dosage of UV light to air, surfaces, objects, and/or reference tags. For example, the light source 204 may provide a dosage of UV light to objects and/or surfaces that may not be reachable by the light source 104.

As shown in FIG. 11, the second actuated mobile device (e.g., actuated mobile device 200 shown in FIG. 11) may smaller than the actuated mobile device (e.g., actuated mobile device 100 shown in FIG. 11).

In some implementations, the actuated mobile device may transmit, from a communications interface (e.g., network interface 116), data including the one or more first surfaces and the one or more second surfaces (e.g., surfaces 300, 302, 304 shown in FIGS. 8, 9, 11, and 12; objects 306, 308, 312, 314 shown in FIGS. 8, 9, 11, 12; and/or reference tag 310 shown in FIG. 9) that have received the first dosage.

In some implementations, the method 10 may include outputting a second dosage of UV light from the at least one light source (e.g., light source 104 shown in FIG. 5) for at least a second portion of the predetermined area that is for a different dosage level.

Figure 3:
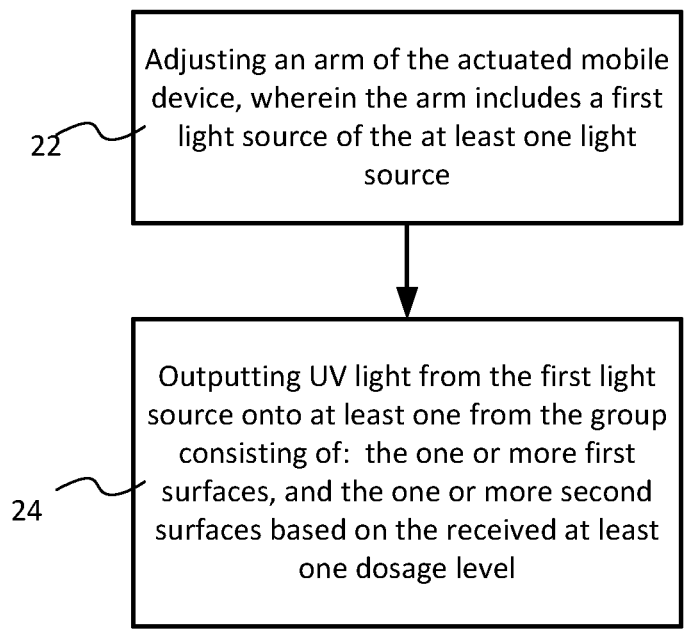
FIG. 3 shows the example method of FIG. 1 may include a method of adjusting an arm of actuated mobile device, where the arm includes another light source to output UV light according to an implementation of the disclosed subject matter.

FIG. 3 shows that the example method of FIG. 1 may include a method of adjusting an arm of actuated mobile device, where the arm includes another light source to output UV light according to an implementation of the disclosed subject matter. At operation 22, the actuated mobile device may adjust an arm (e.g., arm 124 shown in FIG. 10) of the actuated mobile device. The arm may include a light source (e.g., light source 126 shown in FIG. 10). At operation 24, the light source may output UV light onto the one or more first surfaces and/or the one or more second surfaces (e.g., surfaces 300, 302, 304 shown in FIGS. 8, 9, 11, and 12; objects 306, 308, 312, 314 shown in FIGS. 8, 9, 11, 12; and/or reference tag 310 shown in FIG. 9) based on the received at least one dosage level. In some implementations, the light source 126 may be controlled to emit UV light. In some implementations, the light source 126 may be used to provide a dosage of UV light to air, objects, surfaces, reference tags, or the like that the light source 104 may not have provided a dosage of UV light for.

In some implementations, a communications interface (e.g., network interface 116 shown in FIG. 13) of the actuated mobile device may receive a control signal to control movement of the actuated mobile device outside a door to the predetermined area. For example, the actuated mobile device 100 may receive a control signal via the network interface 116 shown in FIG. 13, and the drive system 108 may move the actuated mobile device 100 outside the door 305 of room 210. The control signal may be based on a video signal transmitted by the communication interface of the actuated mobile device. That is, the sensor 102, 106 of the actuated mobile device 100 may capture video, and transmit it via the network 130 (shown in FIG. 14) using the network interface 116. The network interface 116 may receive the control signal for the drive system 108 via the network 130 from, for example, the server 130 and/or remote platform 160.

Figure 4:
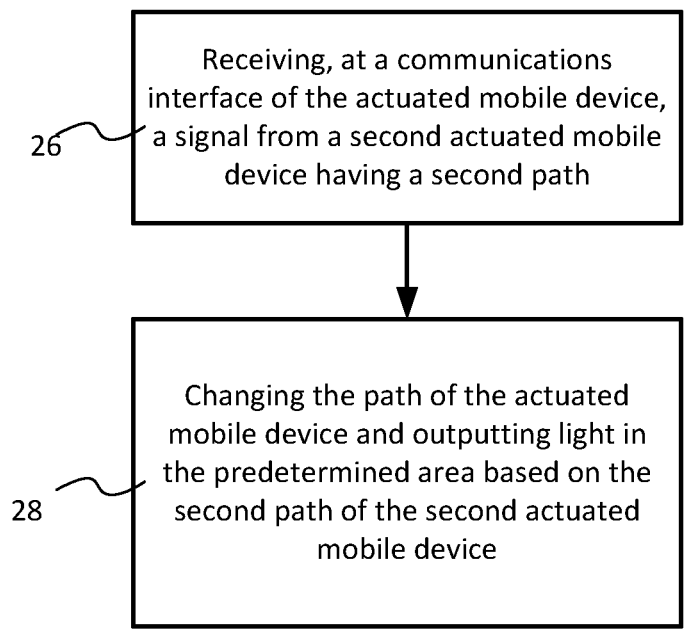
FIG. 4 shows the example method of FIG. 1 may include a method of changing a path of the actuated mobile device when a second actuated mobile device is present within the predetermined area according to an implementation of the disclosed subject matter.

FIG. 4 shows that the example method 10 of FIG. 1 may include a method of changing a path of the actuated mobile device when a second actuated mobile device is present within the predetermined area according to an implementation of the disclosed subject matter. At operation 26, the communications interface (e.g., network interface 116 shown in FIG. 13) of the actuated mobile device (e.g., actuated mobile device 100 shown in FIG. 12) may receive a signal from a second actuated mobile device (e.g., actuated mobile device 200 shown in FIG. 12) having a second path. At operation 28, the path of the actuated mobile device (e.g., actuated mobile device 100) may be changed, and UV light output by the light source (e.g., light source 104) may be output in the predetermined area based on the second path of the second actuated mobile device (e.g., actuated mobile device 200 shown in FIG. 12).

Figure 12:
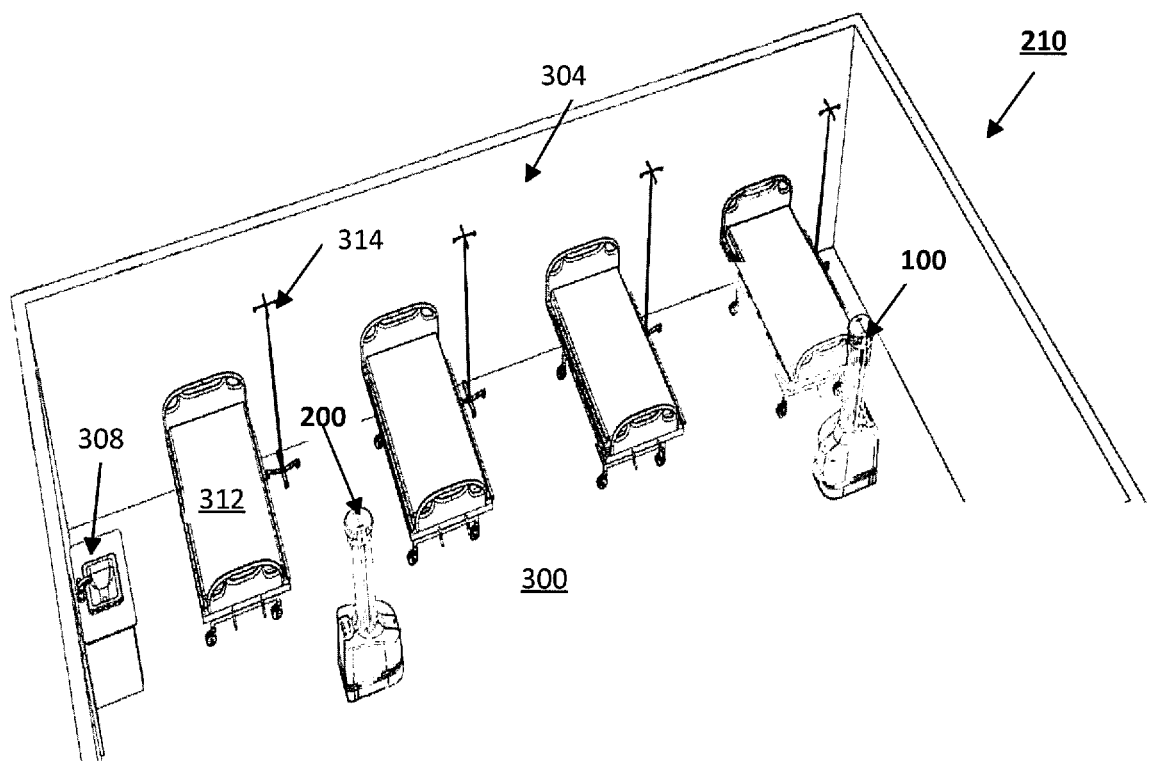
FIG. 12 shows an arrangement where a plurality of actuated mobile devices may have different paths to apply dosages of UV light in the predetermined area according to an implementation of the disclosed subject matter.

That is, in some implementations, an arrangement where actuated mobile device 100 and actuated mobile device 200 may be operated in respective paths in room 210 is shown in FIG. 12. The actuated mobile device 100 may have light source 104, and actuated mobile device 200 may have a similar UV light source. The actuated mobile device 100 may receive a signal from the actuated mobile device 200 with the network interface 116, and may generate and/or adjust a path. The actuated mobile device 100 and the actuated mobile device 200 may have different respective paths in the room 210 to apply dosages of UV light to air, objects, surfaces, and/or reference tags in the room 210. Such objects, surfaces, and the like within the room 210 may more quickly have dosages of UV light applied to them when the actuated mobile devices 100, 200 having different paths move within the room 210.

In some implementations, the actuated mobile device may detect air, surfaces, and/or objects of an area to disinfect them with the UV light as shown in FIG. 9. For example, sensors 102 and/or 106 of the actuated mobile device 100 may be used to detect surface 300 (e.g., a floor of the area), surface 302 and/or surface 306 (e.g., a wall of the area). The sensors 102 and/or 106 may be used to detect object 306 (e.g., a mirror), object 308 (e.g., a sink), and/or reference tag 310. The reference tag 310 may have a first state, and may change to a second state when a dosage of UV light is applied to the reference tag 310. In some implementations, the reference tag 310 may be a virtual reference tag that is represented in a map of the area, which may changes states when UV light is applied to the area that corresponds with the mapped area. In some implementations, the processor may determine that one or more of the objects 306, 308 are hotspots. UV light may be emitted by the light source 104 to disinfect the surfaces 300, 302, 304 and/or the objects 306, 308. The map and the exposure plot may be generated by the processor of the actuated mobile device 100.

Figure 5:
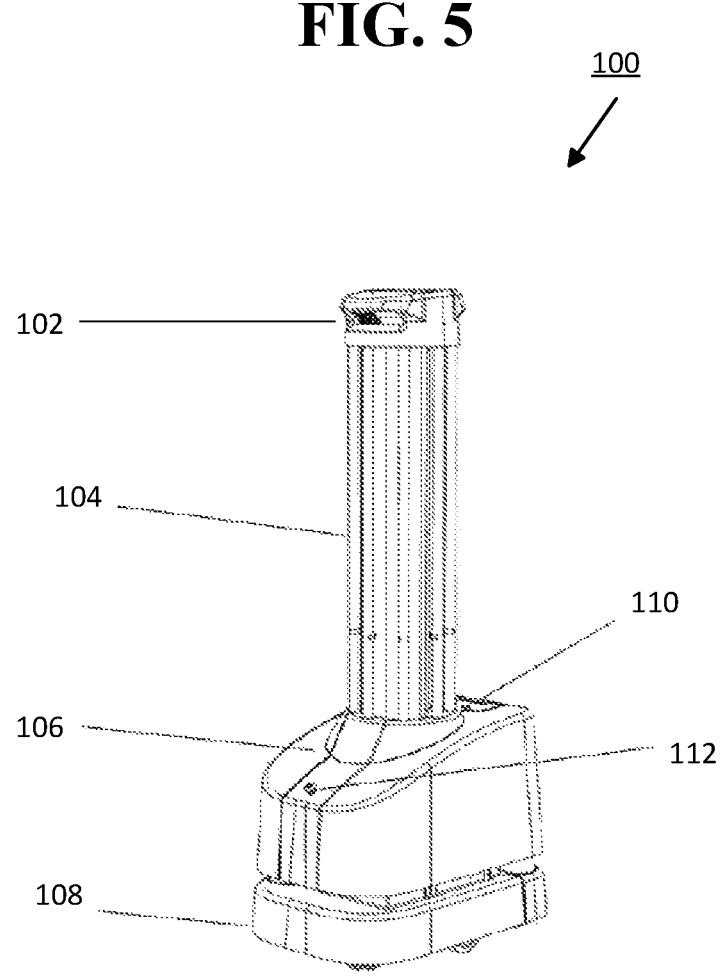
FIGS. 5-7 show a plurality of external views of the actuated mobile device having sensors to detect surfaces and objects in an area, and a light source to output UV light according to implementations of the disclosed subject matter.
Figure 6:
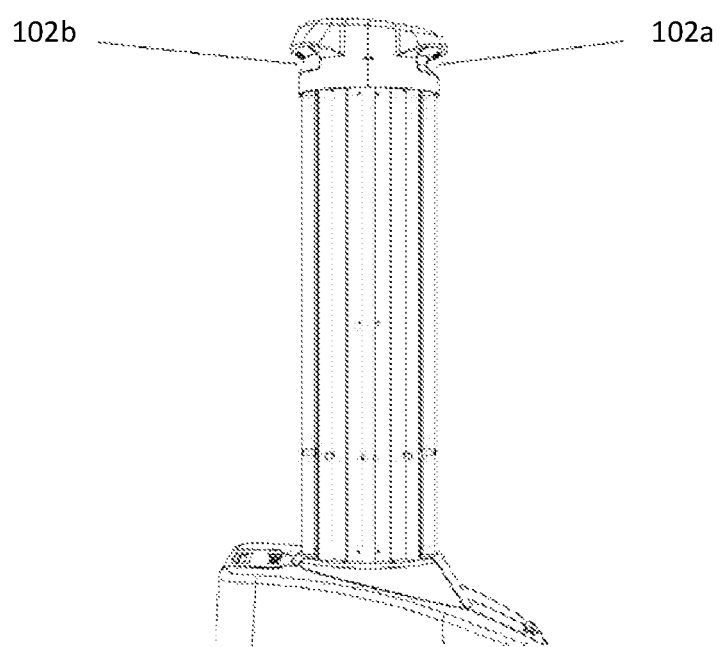
Figure 7:
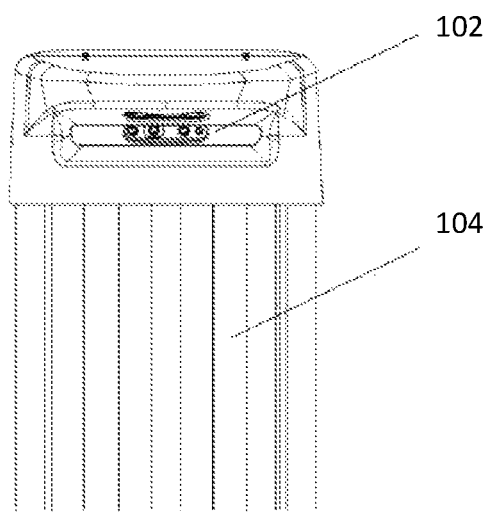

FIGS. 5-7 show a plurality of external views of an actuated mobile device 100 that includes sensors to detect surfaces and objects in an area, and a light source to output UV light having a first dosage based on a received dosage level to disinfect the air, objects, and/or surfaces in the area according to implementations of the disclosed subject matter. The actuated mobile device 100 may include at least a first sensor 102 (shown as sensor 102a and 102b in FIG. 3), a light source 104 to output ultraviolet light, at least a second sensor 106, a drive system 108, a user interface 110, and/or a stop button 112. A controller (e.g., controller 114 shown in FIG. 12 and described below) may be communicatively coupled to the at least one first sensor 102, the light source 104, the at least one second sensor 106, the drive system 108, the user interface 110 and the stop button 112, may control the operations of the actuated mobile device 100.

The at least one first sensor 102 (including sensors 102a, 102b shown in FIG. 3) may determine at least one of an orientation of the actuated mobile device 100 (e.g., a direction that a front side and/or a first side of a robot is facing), a location of the actuated mobile device 100 (e.g., a location of the actuated mobile device 100 in an area), and/or when the light source 104 is within a predetermined distance of a surface and/or object in the area (e.g., surface 300, 302, and/or 304, and/or object 306, 308 shown in FIG. 5). In some implementations, the first sensor 102 may detect air, a surface, a reference tag, and/or objects that may disinfected with UV light from the light source 104.

In some implementations, the at least one first sensor 102 may have a field of view of 70 degrees diagonally. The at least one sensor 102 may have a detection distance of 0.2-4 meters. As shown in FIGS. 5-7, the at least one first sensor 102 may be disposed over the light source 104.

The at least one first sensor 102 may include a first side sensor disposed on a first side of the actuated mobile device 100 and a second side sensor that may be disposed on a second side of the device. For example, as shown in FIG. 6, sensor 102a may be disposed on a first side (e.g., a front side) of the actuated mobile device 100, and sensor 102b may be disposed on a second side (e.g., a back side) of the actuated mobile device 100. Although sensors on two sides of the robot are shown in FIG. 6, there may be a plurality of sensors disposed on different sides of the actuated mobile device 102 to at least detect surfaces and/or objects. In some implementations, sensor 102a and/or sensor 102b may be disposed over the light source 104.

The light source 104 may be one or more bulbs, one or more lamps, and/or an array of light emitting diodes (LEDs) or organic light emitting diodes (OLEDs) to emit UV light (e.g., light having a wavelength of 10 nm-400 nm). The dosage of the UV light (e.g., intensity, duration, optical power output, or the like) may be controlled by the controller 114, which may also turn on or off a portion or all of the devices (e.g., bulbs, lamps, LEDs, OLEDs) of the light source 104. The light source may be controlled to emit UV light when the actuated mobile device is within an area, as the actuated mobile device moves within the area, before the mapping of the area, during the mapping of the area, and/or after the mapping of the area.

In some implementations, the actuated mobile device may include a secondary light source, such as light source 126 which may be coupled to a robotic arm 124 of the actuated mobile device 100. The light source 126 may emit UV light from one or more bulbs, one or more lamps, and/or an array of light emitting diodes (LEDs) or organic light emitting diodes (OLEDs) to emit UV light (e.g., light having a wavelength of 10 nm-400 nm). The light source 126 may be controlled to emit UV light. In some implementations, the light source 126 may be used to provide a dosage of UV light to air, objects, surfaces, reference tags, or the like that the light source 104 may not have provided a dosage of UV light for. Movement of the arm 124 may be controlled by the controller 114 shown in FIG. 13.

Figure 13:
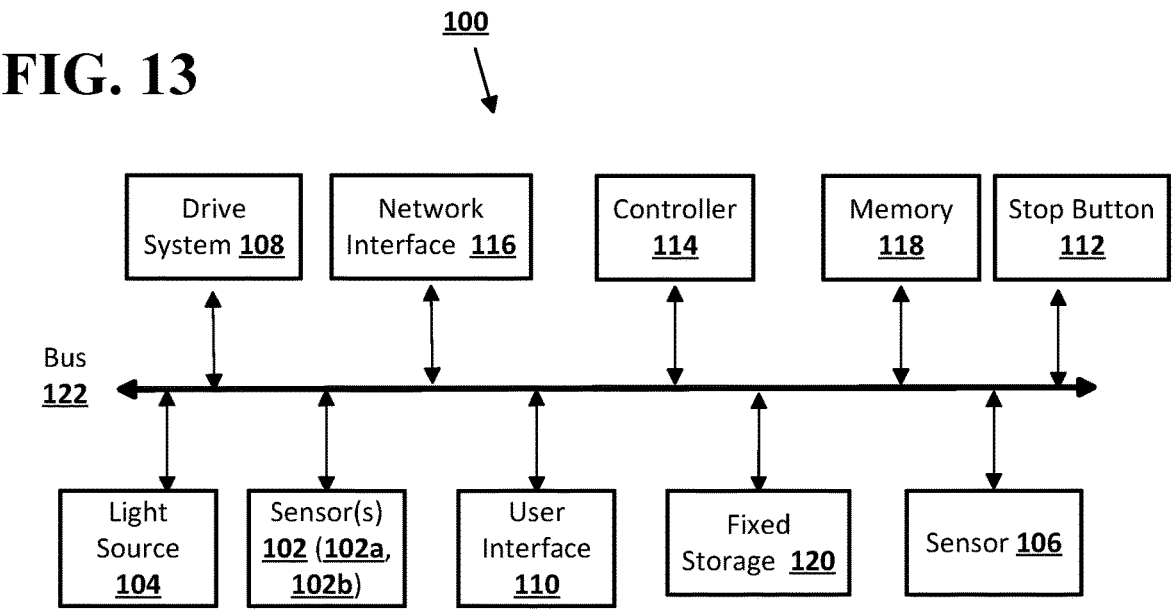
FIG. 13 shows an example configuration of the actuated mobile device of FIGS. 5-7 according to an implementation of the disclosed subject matter.
Figure 14:
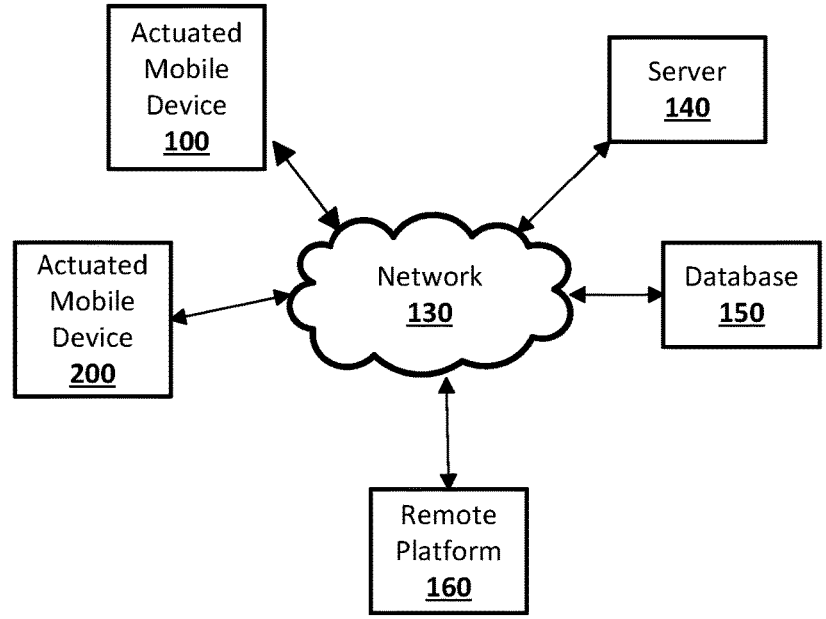
FIG. 14 shows a network configuration which may include a plurality of actuated mobile devices according to implementations of the disclosed subject matter.

The at least one second sensor 106 may be communicatively coupled to the controller 114 shown in FIG. 13, and may be used to detect air, surfaces, and/or objects that may be mapped and/or disinfected with UV light from the light source 104. In some implementations, the at least one second sensor 106 may determine at least one of an orientation of the actuated mobile device 100 (e.g., a direction that a front side and/or a first side of a robot is facing), a location of the actuated mobile device 100 (e.g., a location of the actuated mobile device 100 in an area), and/or when the light source 104 is within a predetermined distance of a surface and/or object in the area (e.g., surface 300, 302, and/or 304, and/or object 306, 308 shown in FIG. 9).

In some implementations, the sensor 102, 106 may be a time-of-flight sensor, an ultrasonic sensor, a two-dimensional (2D) Light Detection and Ranging (LiDAR) sensor, a three-dimensional (3D) LiDAR sensor, and/or a radar (radio detection and ranging) sensor, a stereo vision sensor, 3D three camera, a structured light camera, or the like. The sensor 106 may have a field of view of 20-27 degrees. In some implementations, the sensor 106 may have a detection distance of 0.05-4 meters.

The actuated mobile device 100 may include a motor to drive the drive system 108 to move the actuated mobile device in an area, such as a room, a building, or the like. The drive system 108 may include wheels, which may be adjustable so that the drive system 108 may control the direction of the actuated mobile device 100.

In some implementations, the actuated mobile device 100 may include a base with the drive system 108, and the sensor 102, 106 may be disposed on the base.

The controller 114 may control and/or operate the actuated mobile device 100 in an operation mode which may be a manual mode, an autonomous mode, and/or a tele-operation mode. In the manual mode, the controller 114 may receive on or more control signals from the user interface 110 and/or the stop button 112. For example, a user may control the movement, direction, and/or stop the motion of the actuated mobile device 100 by making one or more selections on the user interface 110. The stop button 112 may be an emergency stop (ESTOP) button which may stop all operations and/or movement of the actuated mobile device 100 when selected. In some implementations, the controller 114 may receive at least one control signal via a network interface 116 (shown in FIG. 13) when operating when operating in the tele-operation mode. For example, the network interface may receive control signals via network 130 from server 140, database 150, and/or remote platform 160, as described below in connection with FIG. 14.

In some implementations, when the actuated mobile device 100 is moving in a direction, the sensor 102, 106 may detect a geometry of one or more surfaces (e.g., surfaces 300, 302, 304 shown in FIG. 9), objects (e.g., objects 306, 308 shown in FIG. 9), and/or reference tags (e.g., reference tag 310 shown in FIG. 9). The output of the at least one first sensor 102 may be, for example, a point cloud of the one or more objects in the path of the actuated mobile device 100. When the sensor 102 and/or sensor 106 is a stereo vision sensor, images from two sensors (i.e., where the two sensors may be part of the stereo vision sensor of the sensor 102 and/or sensor 106) within a known distance from one another distance may be captured at a predetermined point in time, and/or at predetermined time intervals with a global shutter. The global shutter may be configured so that the two sensors of the stereo vision sensor may capture images about simultaneously. One or more features (e.g., surfaces 300, 302, 304, and/or objects 306, 308, and/or reference tag 310 shown in FIG. 9) may be determined from the captured images, and be compared to one another to determine portions that are matching. As the focal length of the two sensors of the stereo vision sensor and the distance between the two sensors (e.g., about 6 cm) may be stored in memory 118 and/or fixed storage 120 (shown in FIG. 13), the controller 114 and/or the at least one first sensor 102 may use the captured images and the stored values to determine the distance from the sensor 102, 106 to the surfaces and/or objects, and may be used by the processor for outputting a dosage of UV light from the light source. In some implementations, the sensor 102, 106 may include at least one laser, LED, and/or OLED, to radiate one or more points on surfaces of objects, when the objects may be without identifying features (e.g., blank walls).

When detecting the surface and/or object, the sensor 102, 106 may be a time-of-flight (TOF) sensor. At least one photon of light may be output by the sensor 102, 106, and may be transmitted through the air. When the at least one photon of light radiates surface and/or an object, a portion of the light may be reflected by the surface and/or the object may return to a receiver portion of the sensor 102, 106. The sensor 106 may calculate the time between sending the at least one photon of light and receiving the reflection, and multiply this value by the speed of light in air, to determine the distance between the sensor 102, 106 and surface and/or object. This may be used to generate the map of the area that the actuated mobile device is operating within.

FIG. 13 shows example components of the actuated mobile device 100 suitable for providing the implementations of the disclosed subject matter. The actuated mobile device 100 may include a bus 122 which interconnects major components of the actuated mobile device 100, such as the drive system 108, a network interface 116 operable to communicate with one or more remote devices via a suitable network connection, the controller 114, a memory 118 such as Random Access Memory (RAM), Read Only Memory (ROM), flash RAM, or the like, the stop button 112, the light source 104, the at least one first sensor 102, a user interface 110 that may include one or more controllers and associated user input devices such as a keyboard, touch screen, and the like, a fixed storage 120 such as a hard drive, flash storage, and the like, and the at least one second sensor 106.

The bus 122 allows data communication between the controller 114 and one or more memory components, which may include RAM, ROM, and other memory, as previously noted. Typically RAM is the main memory into which an operating system and application programs are loaded. A ROM or flash memory component can contain, among other code, the Basic Input-Output system (BIOS) which controls basic hardware operation such as the interaction with peripheral components. Applications resident with the actuated mobile device 100 are generally stored on and accessed via a computer readable medium (e.g., fixed storage 120), such as a solid state drive, hard disk drive, an optical drive, solid state drive, or other storage medium.

The network interface 116 may provide a direct connection to a remote server (e.g., server 140, database 150, and/or remote platform 160 shown in FIG. 13) via a wired or wireless connection (e.g., network 130 shown in FIG. 13). The network interface 116 may provide such connection using any suitable technique and protocol as will be readily understood by one of skill in the art, including digital cellular telephone, WiFi, Bluetooth®, near-field, and the like. For example, the network interface 116 may allow the actuated mobile device 100 to communicate with other computers via one or more local, wide-area, or other communication networks, as described in further detail below. The actuated mobile device may transmit data via the network interface to the remote server that may include a path of operation, the surfaces and/or areas radiated with UV light, and the like.

Many other devices or components (not shown) may be connected in a similar manner. Conversely, all of the components shown in FIG. 13 need not be present to practice the present disclosure. The components can be interconnected in different ways from that shown. Code to implement the present disclosure can be stored in computer-readable storage media such as one or more of the memory 118, fixed storage 120, or on a remote storage location.

FIG. 14 shows an example network arrangement according to an implementation of the disclosed subject matter. Actuated mobile device 100 described above, and/or a similar actuated mobile device 200 may connect to other devices via network 130. The network 130 may be a local network, wide-area network, the Internet, or any other suitable communication network or networks, and may be implemented on any suitable platform including wired and/or wireless networks. The actuated mobile device 100 and/or actuated mobile device 200 may communicate with one another, and/or may communicate with one or more remote devices, such as server 140, database 150, and/or remote platform 160. The remote devices may be directly accessible by the actuated mobile device 100, 200 or one or more other devices may provide intermediary access such as where a server 140 provides access to resources stored in a database 150. The actuated mobile device 100, 200 may access remote platform 160 or services provided by remote platform 160 such as cloud computing arrangements and services. The remote platform 160 may include one or more servers 140 and/or databases 150.

More generally, various implementations of the presently disclosed subject matter may include or be embodied in the form of computer-implemented processes and apparatuses for practicing those processes. Implementations also may be embodied in the form of a computer program product having computer program code containing instructions embodied in non-transitory and/or tangible media, such as solid state drives, DVDs, CD-ROMs, hard drives, USB (universal serial bus) drives, or any other machine readable storage medium, such that when the computer program code is loaded into and executed by a computer, the computer becomes an apparatus for practicing implementations of the disclosed subject matter. Implementations also may be embodied in the form of computer program code, for example, whether stored in a storage medium, loaded into and/or executed by a computer, or transmitted over some transmission medium, such as over electrical wiring or cabling, through fiber optics, or via electromagnetic radiation, such that when the computer program code is loaded into and executed by a computer, the computer becomes an apparatus for practicing implementations of the disclosed subject matter. When implemented on a general-purpose microprocessor, the computer program code segments configure the microprocessor to create specific logic circuits.

In some configurations, a set of computer-readable instructions stored on a computer-readable storage medium may be implemented by a general-purpose processor, which may transform the general-purpose processor or a device containing the general-purpose processor into a special-purpose device configured to implement or carry out the instructions. Implementations may include using hardware that has a processor, such as a general purpose microprocessor and/or an Application Specific Integrated Circuit (ASIC) that embodies all or part of the techniques according to implementations of the disclosed subject matter in hardware and/or firmware. The processor may be coupled to memory, such as RAM, ROM, flash memory, a hard disk or any other device capable of storing electronic information. The memory may store instructions adapted to be executed by the processor to perform the techniques according to implementations of the disclosed subject matter.

The foregoing description, for purpose of explanation, has been described with reference to specific implementations. However, the illustrative discussions above are not intended to be exhaustive or to limit implementations of the disclosed subject matter to the precise forms disclosed. Many modifications and variations are possible in view of the above teachings. The implementations were chosen and described in order to explain the principles of implementations of the disclosed subject matter and their practical applications, to thereby enable others skilled in the art to utilize those implementations as well as various implementations with various modifications as may be suited to the particular use contemplated.

The invention claimed is:

1. A method comprising:
receiving, at an actuated mobile device, at least one dosage level for a predetermined area, wherein the at least one dosage level is based on a first dosage of ultraviolet (UV) light to be output from at least one light source for at least a portion of the predetermined area;
moving the actuated mobile device in a path within the predetermined area and outputting the UV light from the at least one light source onto one or more first surfaces based on the received at least one dosage level;
moving the actuated mobile device within the path, and outputting the UV light onto one or more second surfaces based on the received at least one dosage level;
receiving, at a communications interface of the actuated mobile device, a signal from a second actuated mobile device having a second path; and
changing the path of the actuated mobile device and outputting light in the predetermined area based on the second path of the second actuated mobile device.

2. The method of claim 1, further comprising:
determining, using a processor communicatively coupled to the actuated mobile device, the path of the actuated mobile device.

3. The method of claim 2, wherein the determined path is a random path.

4. The method of claim 2, wherein the path is determined based on at least one from the group consisting of: an environment of the predetermined area, providing a reduced time for disinfection of the predetermined area, increasing the dosage to the one or more first surfaces and the one or more second surfaces.

5. The method of claim 2, wherein the path is determined based at least in part on a two dimensional map or a three-dimensional map generated by the processor and at least one sensor of the actuated mobile device moving within the predetermined area at a previous point in time.

6. The method of claim 2, wherein the path is determined based on an amount of UV light that is to be output on the one or more first surfaces and the one or more second surfaces.

7. The method of claim 1, wherein the path is a perimeter of the predetermined area.

8. The method of claim 1, wherein moving the actuated mobile device within the path comprises:
moving, within the predetermined area, the actuated mobile device in a predetermined pattern.

9. The method of claim 1, further comprising:
determining, using a processor communicatively coupled to the actuated mobile device, whether the one or more first surfaces and the one or more second surfaces have received the first dosage.

10. The method of claim 1, further comprising:
detecting, using a sensor of the actuated mobile device, at least one hotspot within the predetermined area, wherein the at least one hotspot comprises at least one selected from the group consisting of: a predetermined object, at least a portion of the predetermined area, and an object having a predetermined type of contaminant.

11. The method of claim 10, wherein the at least one hotspot is selected from a group consisting of: a chair, a seat, a bed, a sink, mirror, a door, a door handle, a wall, a floor, a ceiling, a shelf, a surface of a table, and any object or surface defined as the at least one hotspot in a memory that is communicatively coupled to a processor of the actuated mobile device.

12. The method of claim 10, further comprising:
outputting the UV light from the at least one light source at a second dosage onto the at least one hotspot, wherein the second dosage is greater than the first dosage.

13. A method comprising:
receiving, at an actuated mobile device, at least one dosage level for a predetermined area, wherein the at least one dosage level is based on a first dosage of ultraviolet (UV) light to be output from at least one light source for at least a portion of the predetermined area;
moving the actuated mobile device in a path within the predetermined area and outputting the UV light from the at least one light source onto one or more first surfaces based on the received at least one dosage level; and
moving the actuated mobile device within the path, and outputting the UV light onto one or more second surfaces based on the received at least one dosage level;
determining, using a processor communicatively coupled to the actuated mobile device, a portion of the one or more first surfaces and the one or more second surfaces that have not received the first dosage; and
performing at least one selected from the group consisting of: reflecting, using an optically reflective surface disposed on a second actuated mobile device operating within the predetermined area, the UV light output by the at least one light source of the actuated mobile device to the determined portions of the one or more first surfaces and the one or more second surfaces; and
emitting UV light from a light source of the second actuated mobile device to the determined portions of the one or more first surfaces and the one or more second surfaces,
wherein the second actuated mobile device is smaller than the actuated mobile device.

14. The method of claim 1, further comprising:
transmitting, from a communications interface of the actuated mobile device, data including the one or more first surfaces and the one or more second surfaces that have received the first dosage.

15. The method of claim 1, further comprising:
outputting a second dosage of UV light from the at least one light source for at least a second portion of the predetermined area that is for a different dosage level.

16. The method of claim 1, further comprising:
adjusting an arm of the actuated mobile device, wherein the arm includes a first light source of the at least one light source; and
outputting UV light from the first light source onto at least one from the group consisting of: the one or more first surfaces, and the one or more second surfaces based on the received at least one dosage level.

17. The method of claim 1, further comprising:
receiving, at a communications interface of the actuated mobile device, a control signal to control movement of the actuated mobile device outside a door to the predetermined area.

18. The method of claim 17, wherein the control signal is based on a video signal transmitted by the communication interface of the actuated mobile device.

* * * * *